(12) United States Patent
Breton et al.

(10) Patent No.: US 10,456,086 B2
(45) Date of Patent: Oct. 29, 2019

(54) METHOD, SYSTEM AND COMPUTER READABLE MEDIUM FOR PREDICTIVE HYPOGLYCEMIA DETECTION FOR MILD TO MODERATE EXERCISE

(71) Applicant: University of Virginia Patent Foundation, Charlottesville, VA (US)

(72) Inventors: Marc D. Breton, Charlottesville, VA (US); Najib Ben-Brahim, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 399 days.

(21) Appl. No.: 15/252,365

(22) Filed: Aug. 31, 2016

(65) Prior Publication Data
US 2018/0055452 A1   Mar. 1, 2018

(51) Int. Cl.
| | |
|---|---|
| G01N 33/48 | (2006.01) |
| A61B 5/00 | (2006.01) |
| A61B 5/0205 | (2006.01) |
| A61B 5/145 | (2006.01) |
| A61M 5/172 | (2006.01) |
| G16H 40/67 | (2018.01) |
| G16H 50/20 | (2018.01) |
| A61B 5/11 | (2006.01) |
| A61M 5/142 | (2006.01) |

(52) U.S. Cl.
CPC .......... *A61B 5/7275* (2013.01); *A61B 5/0205* (2013.01); *A61B 5/14532* (2013.01); *A61B 5/4839* (2013.01); *A61B 5/7264* (2013.01); *A61M 5/1723* (2013.01); *G16H 40/67* (2018.01); *G16H 50/20* (2018.01); *A61B 5/1118* (2013.01); *A61B 5/7225* (2013.01); *A61B 2562/0219* (2013.01); *A61M 2005/14208* (2013.01); *A61M 2205/3303* (2013.01); *A61M 2205/3327* (2013.01); *A61M 2205/35* (2013.01); *A61M 2205/3561* (2013.01); *A61M 2205/505* (2013.01); *A61M 2205/52* (2013.01)

(58) Field of Classification Search
None
See application file for complete search history.

(56) References Cited

U.S. PATENT DOCUMENTS

| | | | |
|---|---|---|---|
| 2011/0054391 A1* | 3/2011 | Ward | A61B 5/14532 604/66 |
| 2013/0109944 A1* | 5/2013 | Sparacino | A61B 5/743 600/365 |
| 2013/0130215 A1* | 5/2013 | Bock | G09B 23/28 434/247 |

OTHER PUBLICATIONS

Keenan et al. (Journal of Diabetes Science and Technology; Sep. 2009, vol. 3, Iss. 5, 1207-1214).*
Pickup et al. (Diabetes Care, Mar. 2002, vol. 25, Num. 3, 593-598).*

* cited by examiner

*Primary Examiner* — Larry D Riggs, II
(74) *Attorney, Agent, or Firm* — Buchanan Ingersoll & Rooney PC

(57) ABSTRACT

A system, method and non-transient computer readable medium for predicting hypoglycemic risk in patients with diabetes following moderate exercise. A system may include a digital processor; and an exercise module configured to generate a hypoglycemia risk signal with a hypoglycemia prediction algorithm and to determine a hypoglycemia risk state with a classifier algorithm that classifies the hypoglycemia risk signal to identify an actionable hypoglycemia risk state based on a predefined threshold.

21 Claims, 6 Drawing Sheets

METHOD, SYSTEM AND COMPUTER READABLE MEDIUM FOR PREDICTIVE HYPOGLYCEMIA DETECTION FOR MILD TO MODERATE EXERCISE

FIELD

A system, method and non-transient computer readable medium for predicting exercise-induced hypoglycemia in patients with diabetes.

BACKGROUND

Regular physical activity has a positive impact on the quality of life and decreases cardiovascular risk factors and mortality. However, fear of hypoglycemia is the strongest barrier to regular exercise in patients with type 1 diabetes. Physical activity has been known for increasing the risk of hypoglycemia for people with type 1 diabetes.

To maintain their blood glucose levels in the normal range, type 1 diabetes patients are required to balance insulin doses and food intake on a regular basis. The exogenous insulin leads to a hyperinsulinemic state during exercise which is due to the absence of a physiological decrease in insulin secretion and an increase in the absorption of previously injected insulin. Hyperinsulinemia, coupled with impaired counterregulatory response and an imbalance between hepatic glucose production and muscle glucose disposal, leads to hypoglycemia.

The fear of hypoglycemia generally leads to overcompensation of additional intake of carbohydrates and/or excessive insulin doses reductions. For better glycemic control actions, patients with type 1 diabetes need to be informed on the risk of hypoglycemia associated with exercise.

There remains a need for a predictive hypoglycemia model for patients with type 1 diabetes who intend to exercise at a moderate intensity level. There also remains a need for a model that can be used as the foundation for a predictive hypoglycemia classifier. There also remains a need for decision support systems to mitigate hypoglycemia risk by, for example, enabling manual and automated adjustments to insulin delivery, recommending carbohydrate consumption, or recommending that exercise be postponed until the risk of exercise-induced hypoglycemia is reduced.

SUMMARY

An aspect of an embodiment of the present invention provides a system, method, and non-transient computer readable medium for, among other things, predicting exercise-induced hypoglycemia in patients prior to exercise.

An aspect of an embodiment of the present invention provides for, among other things, implementing an initial step that may involve obtaining a blood glucose signal and/or an initial glycemic slope signal, which may be obtained from a continuous glucose monitor. See also, for example, U.S. patent application Ser. No. 14/241,383 entitled "Method, System and Computer Readable Medium for Adaptive Advisory Control of Diabetes", filed Feb. 26, 2014; International Patent Application No. PCT/US2012/052422 entitled "Method, System and Computer Readable Medium for Adaptive Advisory Control of Diabetes", filed Aug. 26, 2012; and International Patent Application Publication No. WO 2013/032965, Mar. 7, 2013, all of which are hereby incorporated by reference in their entirety herein (and which are not admitted to be prior art with respect to the present invention by inclusion in this section).

An aspect of various embodiments of the present invention determines a hypoglycemia risk signal with a hypoglycemia prediction algorithm, and determines a hypoglycemia risk state with a classifier algorithm that classifies the hypoglycemia risk signal to identify an actionable hypoglycemia risk state based on a predefined threshold. In various embodiments, the actionably hypoglycemia risk state is a "risk assessment" (i.e., not a probability determination, for example) and enables mitigation opportunities for the user, either through manual or automated methods.

An aspect of various embodiments of the present invention is responsive to an indicated risk of hypoglycemia during and after exercise. In various embodiments, the present invention generates an alert, communicates an instruction to a user, communicates an instruction to an insulin pump, and/or communicate an instruction to a pump containing a glucose increasing drug, responsive to an indicated risk of hypoglycemia during or after exercise.

In various embodiments of the present invention, the hypoglycemia prediction algorithm determines the probability of a user being hypoglycemic during or after exercise based on the blood glucose signal, the ratio of insulin on board over total daily insulin signal, and the initial glycemic slope signal. In various embodiments, the hypoglycemia prediction algorithm also determines the probability of a user being hypoglycemic during or after exercise based on one or more other signals including: the type of exercise, the intensity of exercise, and the duration of exercise to be performed.

In various embodiments, the hypoglycemia prediction algorithm also determines the probability of a user being hypoglycemic during or after exercise based on one or more other signals including: the relative insulin on board (IOB) as an indicator of the remaining insulin in the bloodstream (calculated taking into account the 4 hour insulin injections history and subtracting the basal injections), the absolute insulin on board ($IOB_{abs}$, absolute refers to the fact that all injections are taken into account in the 4 hour insulin injections history), the total daily insulin (TDI), the ratio $IOB_{abs}$/TDI as an indicator of body insulin exposure, the ratio TDI/BW (where BW is the body weight), the age (as a continuous or categorical variable), the body weight (BW) and the gender.

An aspect of an embodiment of the present invention provides a system, method and computer readable medium that, among other things, defines an algorithmic architecture for control of diabetes that includes both live and retrospective analysis of data. See also, for example, U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012; International Patent Application No. PCT/US2010/036629 entitled "System Coordinator and Modular Architecture for Open-Loop and Closed-Loop Control of Diabetes", filed May 28, 2010; and International Patent Application Publication No. WO 2010/138848, Dec. 2, 2010, all of which are hereby incorporated by reference in their entirety herein (and which are not admitted to be prior art with respect to the present invention by inclusion in this section). An aspect of various embodiments of the present invention (system, method and computer readable medium) may provide a number of novel and nonobvious features, elements and characteristics, such as but not limited thereto, as follows: creating and applying algorithms (and techniques and methods) for retrospective analysis. Moreover, such algorithms (and techniques and methods) may be implemented by being integrated (e.g., "plug into") the modular architecture of the system or device.

An aspect of various embodiments of the present invention (system, method and computer readable medium) may provide a number of novel and nonobvious features, elements and characteristics, such as but not limited thereto, the following: (i) it uses CGM (which may in turn be enhanced by knowledge of finger stick values, of which may be optional and not necessarily essential), (ii) it addresses both hypoglycemia and hyperglycemia, (iii) it produces a "risk assessment" (i.e., not a probability determination, for example), (iv) it provides risk assessments that are broken down into (a) "unaddressable risk" where the historical record indicates a tendency to both hypo and hyperglycemia at a given time of the day, (b) actionable hypoglycemia risk, and (c) actionable hyperglycemia risk.

The devices, systems, non-transitory computer readable medium, and methods of various embodiments of the invention disclosed herein may utilize aspects disclosed in "Decision Support System for T1DM patients' safety during and immediately after a mile to moderate physical activity", the attached Appendix 1, and "Predictive Hypoglycemia detection classifier for mild to moderate exercise in type 1 Diabetes", attached as Appendix 2, both of which are hereby incorporated by reference herein in their entirety (and which are not admitted to be prior art with respect to the present invention by inclusion in this section).

BRIEF DESCRIPTION OF THE DRAWINGS

The invention can be best understood from the following detailed description of exemplary embodiments of the invention taken in conjunction with the accompanying drawings.

DETAILED DESCRIPTION OF THE DRAWINGS

Figure 1:
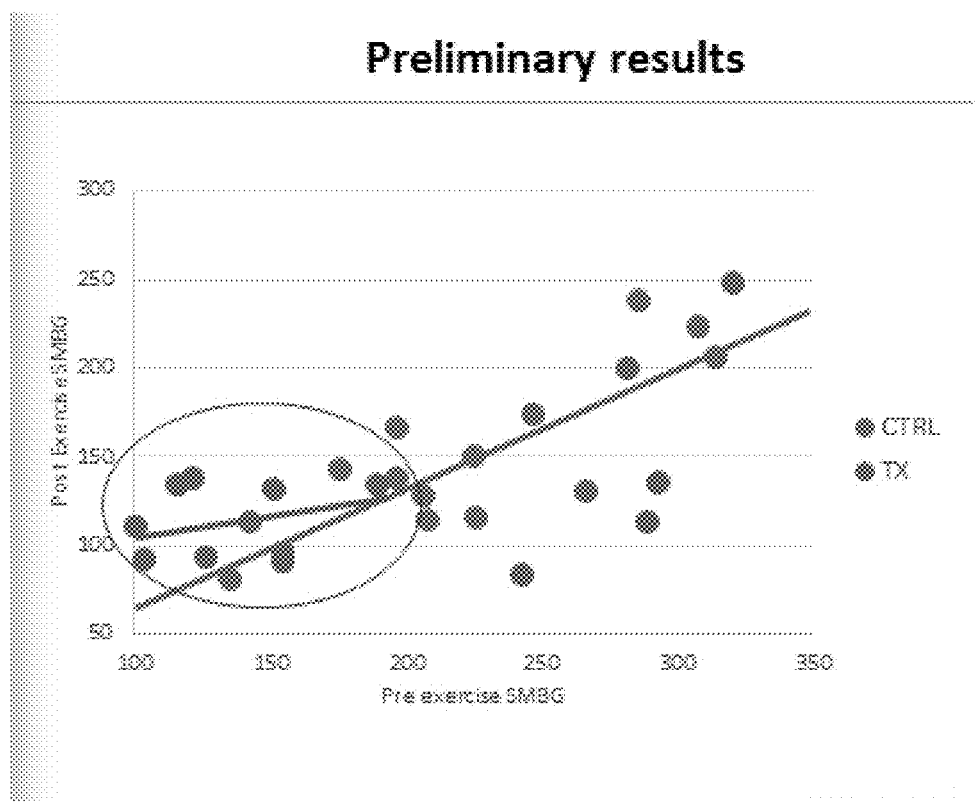
FIG. 1 is a graph of test results for an embodiment of the invention.

This invention provides a method, system, and computer readable medium for, among other things, predicting the hypoglycemic risk for mild to moderate exercise for patients with type 1 diabetes.

In view of the many possible variations within the spirit of the invention, the invention will be discussed with reference to exemplary embodiments. However, it will be appreciated by those skilled in the art that the following discussion is for demonstration purposes, and should not be interpreted as a limitation of the invention. Other variations without departing from the spirit of the invention are applicable.

A method and system for predicting exercise-induced hypoglycemia for a user are presently disclosed. In an embodiment, a system includes a digital processor and an exercise module in communication with the digital processor configured to implement the disclosed method. In some embodiments, the method includes obtaining a blood glucose signal ($BG_{start}$), a ratio of absolute insulin on board over total daily insulin signal ($IOB_{abs}/TDI$), and an initial glycemic slope signal ($S0$). The method also includes determining a hypoglycemia risk signal with a hypoglycemia prediction algorithm that determines the probability of the user being hypoglycemic during or after exercise based on the blood glucose signal, the ratio of absolute insulin on board over total daily insulin signal, and the initial glycemic slope signal; and determining a hypoglycemia risk state with a classifier algorithm that classifies the hypoglycemia risk signal to identify an actionable hypoglycemia risk state based on a predefined threshold.

In an embodiment, the response variable H is obtained by applying a threshold blood glucose level ($BG_{thresh}$) on the actual blood glucose value at the end of exercise ($BG_{end}$).

$$H = \begin{cases} 1, & BG_{end} < BG_{thresh} \\ 0, & BG_{end} \geq BG_{thresh} \end{cases}$$

In one embodiment, the hypoglycemia prediction algorithm is the logit transform of the probability of being hypoglycemic during or after exercise, and is defined by the equation:

$$Logit(P) = \beta_0 + \beta_1 \cdot BG_{start} + \beta_2 \cdot \frac{IOB_{abs}}{TDI} + \beta_3 \cdot S_0$$

$$\text{Where} \begin{cases} Logit(P) = \log\left(\frac{P}{1-P}\right) \\ P = \dfrac{e^{\beta_0 + \beta_1 \cdot BG_{start} + \beta_2 \cdot \frac{IOB_{abs}}{TDI} + \beta_3 \cdot S_0}}{1 + e^{\beta_0 + \beta_1 \cdot BG_{start} + \beta_2 \cdot \frac{IOB_{abs}}{TDI} + \beta_3 \cdot S_0}} \end{cases}$$

In one embodiment, the coefficients $\beta_0$, $\beta_1$, $\beta_2$, $\beta_3$ are 8.682, −0.082, 69.572, and −1.869, respectively. In other embodiments, the hypoglycemia prediction algorithm may include additional or different terms, with different predetermined coefficients such that the hypoglycemia risk signal is based on additional signal as discussed below.

After the hypoglycemia risk signal is determined using the hypoglycemia prediction algorithm, a hypoglycemia risk state is determined using a classifier algorithm. The classifier algorithm identifies an actionable hypoglycemia risk state based on a predefined threshold ($DET_{thresh}$), which may be communicated to the user or used in controlling insulin delivery to mitigate the hypoglycemic risk.

In one embodiment, a the classifier algorithm is:

$$Logit(P) = \begin{cases} 1, & Logit(P) \geq DET_{thresh} \\ 0, & Logit(P) < DET_{thresh} \end{cases}$$

With this classifier algorithm a value of 1 indicates a risk of hypoglycemia following the intended exercise. In one embodiment, the DETthresh is 0.4.

In other embodiments, the classifier algorithm may classify two or more actionable hypoglycemia risk states, each having a recommended action for the user, such as, reducing or stopping insulin delivery, consuming a defined amount of carbohydrates, or postponing the intended exercise.

In various embodiments, an alert is generated if the hypoglycemia risk state indicates a risk of hypoglycemia during or after exercise. The alert may be a visual or audible alert. In one embodiment, the alert is displayed on the display of a portable computing device. In other embodiments, the alert may be communicated to the user through email, text message, or other methods as desired.

In yet another embodiments, if the hypoglycemia risk state indicates a risk of hypoglycemia during or after exercise, an instruction is communicated to an insulin pump. In one example, the instruction causes the pump to discontinue supplying insulin for a determined period of time to mitigate risk of hypoglycemia during and after the intended exercise.

In yet another embodiment, the user is instructed to consume a determined amount of carbohydrates in order to mitigate the risk of hypoglycemia during or after exercise.

In yet another embodiment, the user is instructed to increase the amount of a glucose increasing drug (e.g. glucagon)

In yet another embodiment, the user or the injection device is presented with a combination of advice signals The disclosed system and method may receive input signals from the user and/or from a variety of sensors. In one embodiment, the blood glucose signal is received from a continuous blood glucose monitor. The initial glycemic slope signal may be obtained based on the received blood glucose signal or may be computed by the continuous blood glucose monitor and provided as a separate signal. In either case, the initial glycemic slope signal identifies the trend of the blood glucose level prior to starting exercise.

A user may employ the disclosed system and method prior to starting exercise in order to assess the risk of being hypoglycemic during or after exercise. In some embodiments, one or more sensors may be used to detect exercise so that a determination of the post-exercise hypoglycemic risk may be provided automatically. In one embodiment, an activity signal is obtained from at least one sensor configured to detect when the user beings to exercise. A heartrate sensor may be used to detect an increase in heartrate associated with exertion related to the beginning of exercise or other physical activity. In some embodiments, an accelerometer, which may include a multi-axis accelerometer may be used to detect movement associated with exercise. In response to detecting that the use has begun to exercise, the hypoglycemia risk state is determined. If the hypoglycemia risk state indicates a risk of hypoglycemia during or after exercise, an alert may be generated and a recommendation provided to the user, such as, discontinue exercise or consume carbohydrates to mitigate the risk of hypoglycemia.

The disclosed system and method may also utilize additional factors to determine the risk of hypoglycemia during or after exercise. A user may provide additional information, such as one or more of the type of exercise, the intensity of the exercise, and the planned duration of the exercise to be performed. In some embodiments, the hypoglycemia prediction algorithm may therefore determine the probability of the user being hypoglycemic during or after exercise based at least in part on this additional information. In yet other embodiments, the classifier algorithm may classify the risk of hypoglycemia based at least in part on this additional information, such as by reducing the predefined threshold at which an actionable risk of hypoglycemia is indicated.

An embodiment of the presently disclosed method was tested, and the results are illustrated in FIG. 1. As shown, the blood glucose levels of multiple patients were measured after exercise (Post exercise SMBG) and plotted versus the patient's blood glucose level prior to exercise (Pre exercise SMBG). The patients were divided into a control group (CNTL), and a test group (TX) utilizing the presently disclosed method. At the time of the exercise, the test subjects used the method to determine a hypoglycemia risk state and received one of our recommendations based on the determined hypoglycemia risk state. The test subjects were instructed to do nothing if a hypoglycemia risk state was not determined, and to stop insulin for two hours if a hypoglycemia risk state was determined.

As shown in FIG. 1, the blood glucose level of the control group declined at a substantially faster rate than the test group. In other words, the determination of hypoglycemia risk state enabled the test group to modify their insulin regime to mitigate the risk of hypoglycemia after moderate exercise. Accordingly, these results demonstrate that the disclosed system and method enables patients with type 1 diabetes to benefit from exercise while reducing the risk of exercise induced hypoglycemia.

Figure 2:
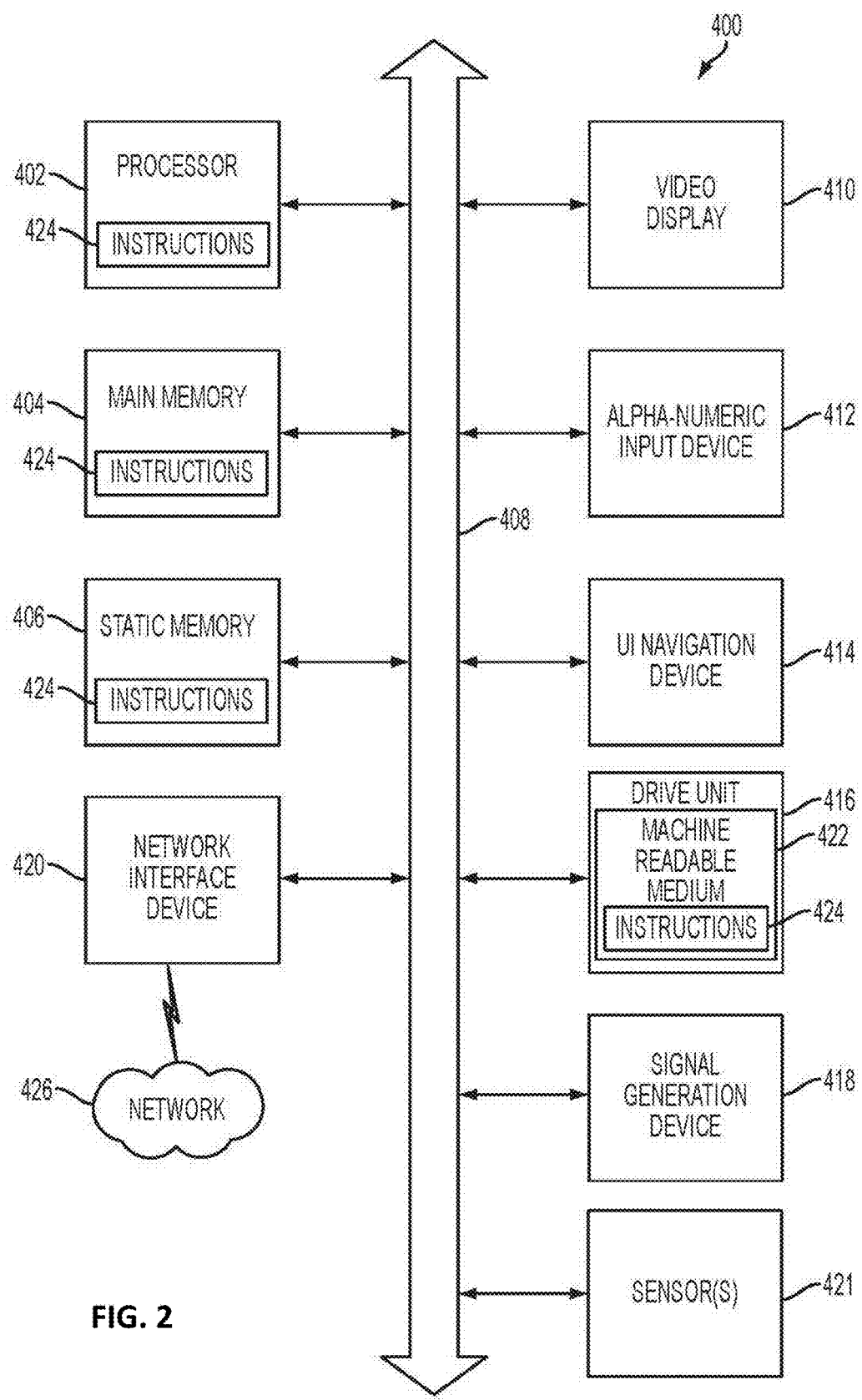
FIG. 2 is a block diagram of an example of a machine upon which one or more aspects of embodiments of the present invention can be implemented.

FIG. 2 is a block diagram illustrating an example of a machine upon which one or more aspects of embodiments of the present invention can be implemented.

FIG. 2 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 810, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Figure 3:
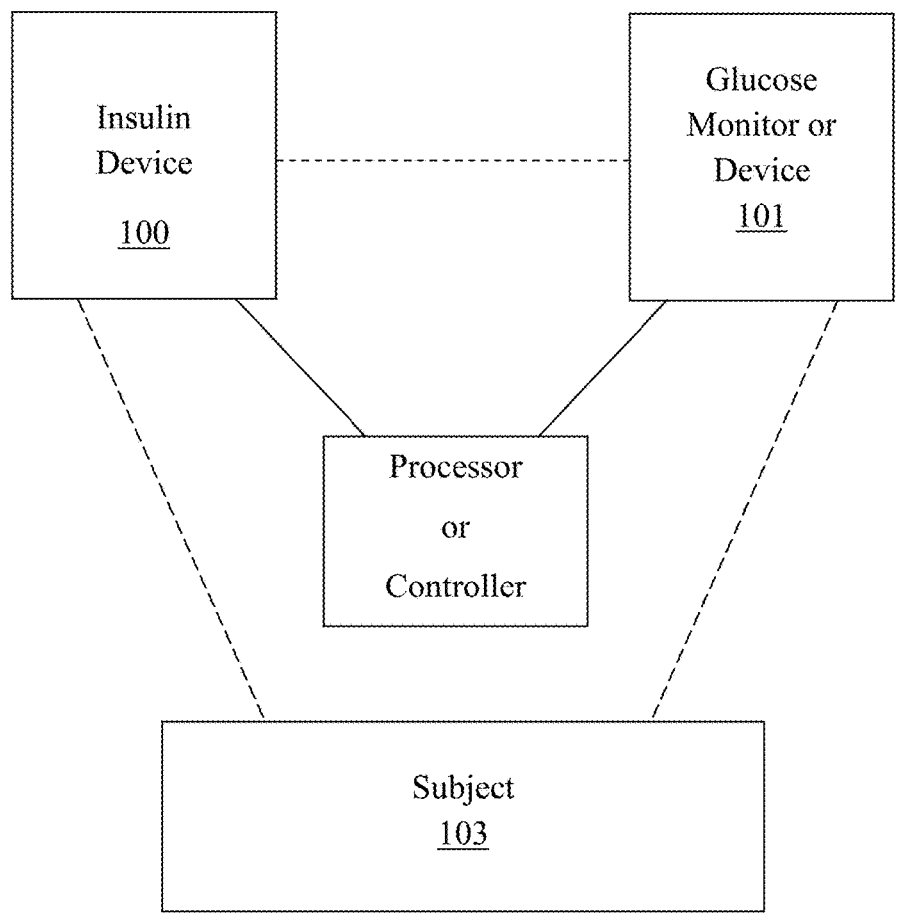
FIG. 3 is a high level functional block diagram of an embodiment of the invention.

FIG. 3 is a high level functional block diagram of an embodiment of the invention.

As shown in FIG. 3, a processor or controller 102 may communicate with the glucose monitor or device 101, and optionally the insulin device 100. The glucose monitor or device 101 may communicate with the subject 103 to monitor glucose levels of the subject 103. The processor or controller 102 is configured to perform the required calculations. Optionally, the insulin device 100 may communicate with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Referring to FIG. 4, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 4A:
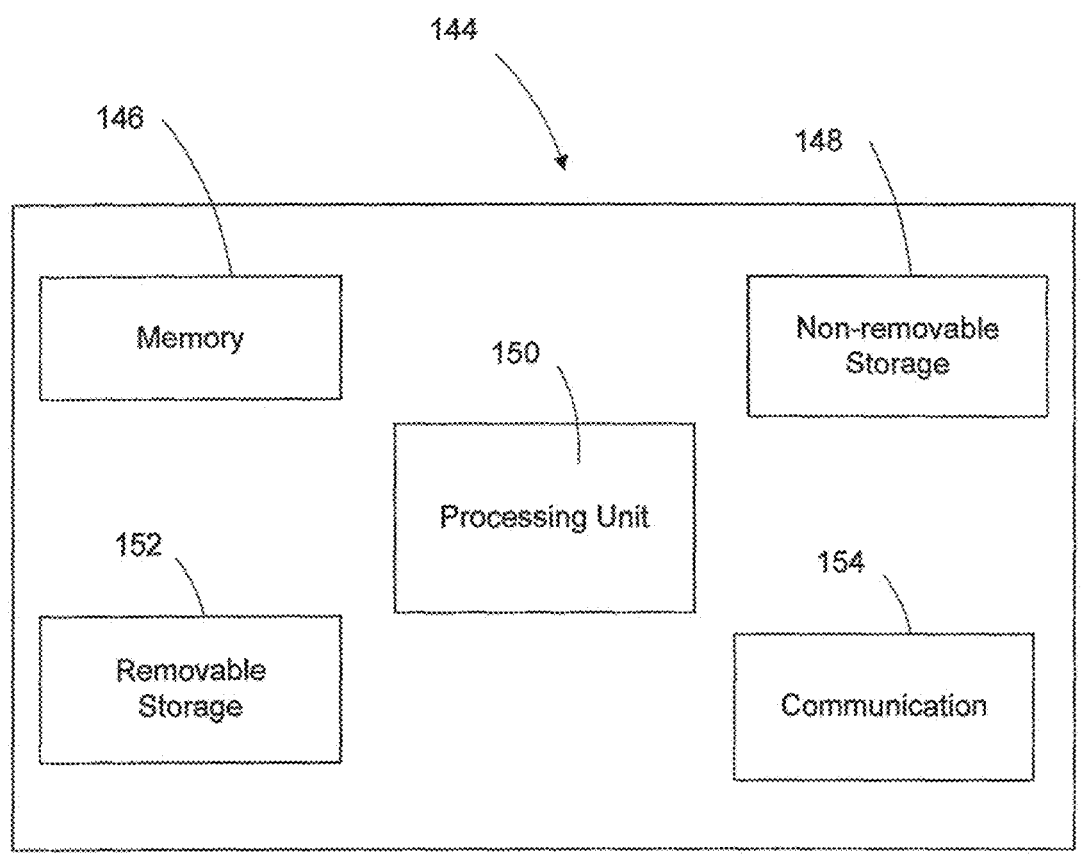
FIG. 4A is a block diagram of a computing device upon which one or more aspects of embodiments of the invention can be implemented.
Figure 4B:
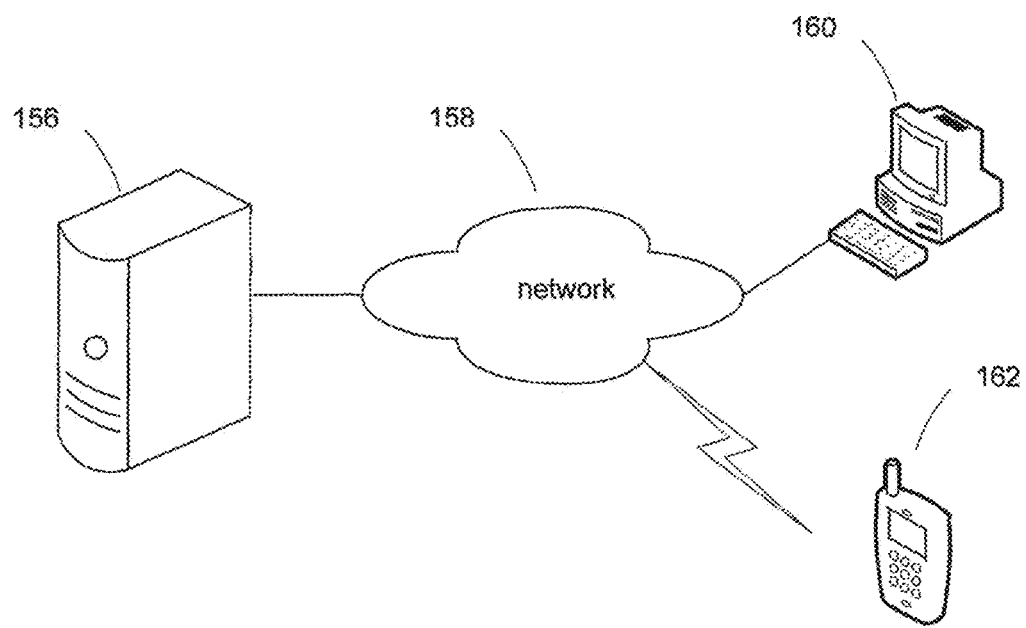
FIG. 4B illustrates a network system upon which one or more aspects of embodiments of the invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 4B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and an insulin device. Any of the components shown or discussed with FIG. 4A may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 5:
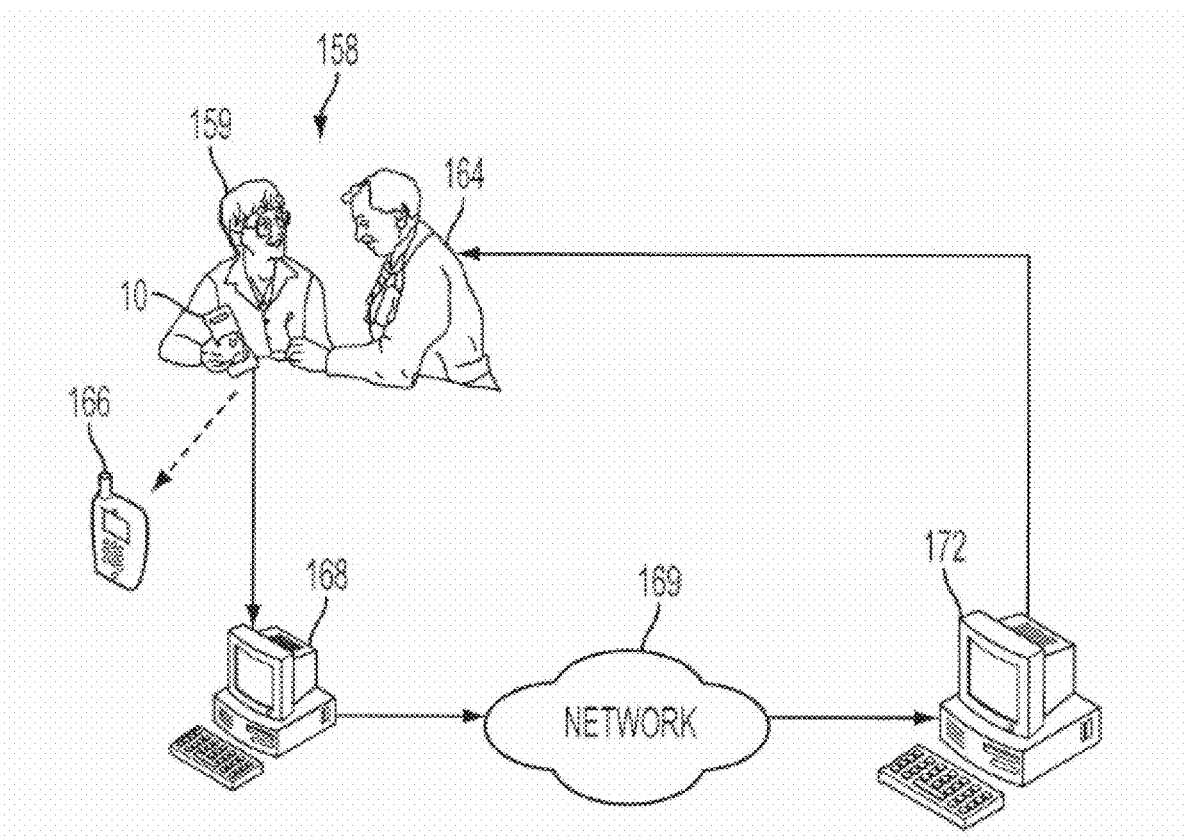
FIG. 5 illustrates a system in which one or more embodiments of the invention can be implemented using a network, or portions of a network or computers.

FIG. 5 illustrates a system in which one or more embodiments of the invention can be implemented using a network, or portions of a network or computers.

FIG. 5 diagrammatically illustrates an exemplary system in which examples of the invention can be implemented. In an embodiment the glucose monitor may be implemented by the subject (or patient) at home or other desired location. However, in an alternative embodiment it may be implemented in a clinic setting or assistance setting. For instance, referring to FIG. 5, a clinic setup 158 provides a place for doctors (e.g. 164) or clinician/assistant to diagnose patients (e.g. 159) with diseases related with glucose. A glucose monitoring device 10 (and/or insulin pump device or pump) can be used to monitor and/or test the glucose levels of the patient. It should be appreciated that while only glucose monitor device 10 is shown in the figure, the system of the invention and any component thereof may be used in the manner depicted by FIG. 5. The system or component may be affixed to the patient or in communication with the patient as desired or required. For example the system or combination of components thereof - including a glucose monitor device 10, a controller 12, or an insulin pump 14, or any other device or component - may be in contact or affixed to the patient through tape or tubing or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and / or glucose monitoring center 172 for performing error analyses. This can provide a centralized accuracy monitoring and/or accuracy enhancement for glucose centers, due to the importance of the glucose sensors.

Examples of the invention can also be implemented in a standalone computing device associated with the target glucose monitoring device. An exemplary computing device in which examples of the invention can be implemented is schematically illustrated in FIG. 4A.

The following patents, applications and publications as listed below and throughout this document are hereby incorporated by reference in their entirety herein (and are not admitted to be prior art with respect to the present invention by inclusion in this section).

[1] Fox K R: The influence of physical activity on mental well-being. Public Health Nutr 2:411-418, 1999

[2] Franco O H, de Laet C, Peeters A, Jonker J, Mackenbach J, Nusselder W: Effects of physical activity on life expectancy with cardiovascular disease. Arch Intern Med165:2355-2360, 2005

[3] Kujala U M, Kaprio J, Sarna S, Koskenvuo M: Relationship of leisure-time physical activity and mortality. JAMA 279:440-444, 1998

[4] A. Brazeau, R. Rabasa-Lohret, I. Strychar, H. Mircescu,Barriers to physical activity among patients with type 1 diabetes, Diabetes Care 31 (2008) 2108-2109.

[5] Riddell M C, Iscoe K E. Physical activity, sport, and pediatric diabetes. Pediatr Diabetes. 2006;7(1):60-70.

[6] Riddell M, Perkins B. Exercise and glucose metabolism in persons with diabetes mellitus: perspectives on the role for continuous glucose monitoring. J Diabetes Sci Technol 2009: 3: 914-923.

[7] Ertl A C, Davis S N 2004 Evidence for a vicious cycle of exercise and hypoglycemia in type 1 diabetes mellitus. Diabetes Metab Res Rev 20:124-130

[8] Cryer P E, Davis S N, Shamoon H 2003 Hypoglycemia in diabetes. Diabetes Care26:1902-1912

[9] Goodyear L J, Kahn B B: Exercise, glucose transport, and insulin sensitivity. Annu Rev Med 1998;49:235-261.

[10] Younk L M, Mikeladze M, Tate D, Davis S N: Exerciserelated hypoglycemia in diabetes mellitus. Expert Rev Endocrinol Metab 2011;6:93-108.

[11] Dohm G L: Invited review: regulation of skeletal muscle GLUT-4 expression by exercise. J Appl Physiol 2002;93: 782-787.

[12] Brazeau A S, Rabasa-Lhoret R, Strychar I, Mircescu H. Barriers to physical activity among patients with type 1 diabetes. Diabetes Care. 2008;31(11):2108-9.

[13] T. Hastie, R. Tibshirani, J. Friedman. The elements of Statistical Learning. Springer series in statistics. Springer, N.Y., 2001.

[14] H. Akaike. A new look at the statistical model identification. IEEE Trans. Autom. Control, AC-19: 716-723, 1974.

[15] Hirotugu Akaike. Fitting autoregressive models for prediction. Annals of the Institute of Statistical Mathematics, 21(1), 1969.

[16] Michele Schiavon, Chiara Dalla Man, Yogish C. Kudva, Ananda Basu, Claudio Cobelli. In Silico Optimization of Basal Insulin Infusion Rate during Exercise: Implication for Artificial Pancreas. J Diabetes Sci Technol November 2013 vol. 7 no. 6 1461-1469.

[17] Kovatchev B P, Breton M, Dalla Man C, Cobelli C. In silico preclinical trials: a proof of concept in closed-loop control of type 1 diabetes. J Diabetes Sci Technol. 2009; 3(1):44-55

[18] Dalla Man C, Micheletto F, Dayu L, Breton M, Kovatchev B P, Cobelli C. The UVA/Padova type 1 diabetes simulator: new features. 2013. J Diabetes Sci Technol.

[19] Paul Berger and Franz Edelman. 1977. IRIS: a transactions-based DSS for human resources management. SIGMIS Database 8, 3 (January 1977), 22-29. DOI=10.1145/1017583.1017588.

[20] Izak Benbasat. 1977. Cognitive style considerations in DSS design. SIGMIS Database 8, 3 (January 1977), 37-38. DOI=10.1145/1017583.1017590.

[21] Green, C., Yates, R., Raphael, B., and Rosen, C. Research in Advanced Formal Theorem-Proving Techniques, Technical Note . AI Center, SRI International, 333 Ravenswood Ave, Menlo Park, Calif. 94025, June 1969.

[22] Richard D. Hackathorn. 1977. Modeling unstructured decision making. SIGMIS Database 8, 3 (January 1977), 41-42. DOI=10.1145/1017583.1017593

[23] Bonczek, Robert H., Clyde W. Holsapple, and Andrew B. Whinston. Foundations of Decision Support Systems. Acad. Press, 1981.

[24] P. Keen, M. Scott Morton, Decision Support Systems: An Organizational Perspective, Addison-Wesley Publishing, Reading, Mass., 1978.

[25] Shim, J. P., Merrill Warkentin, James F. Courtney, Daniel J. Power, Ramesh Sharda, and Christer Carlsson. "Past, Present, and Future of Decision Support Technology." Decision Support Systems, Decision Support System: Directions for the Nest Decade, 33, no. 2 (June 2002): 111-26. doi:10.1016/S0167-9236 (01)00139-7.

[26] Bates D W, Cohen M, Leape L L, Overhage J M, Shabot M M, Sheridan T J, Reducing the frequency of errors in medicine using information technology. Am Med Inform Assoc. 2001 July-August; 8(4):299-308.

[27] "Using an Insulin Pump and a CGM." Diabetes Forecast. Accessed Mar. 21, 2015. http://www.diabetesforecast.org/2013/jan/cgms-and-insulin-pumps-2013.html.

[28] Teich J M, Wrinn M M. Clinical decision support systems come of age. MD Comput. 2000 Jan-Feb; 17(1):43-6.

[29] Bao, L. and S.S. Intille, Activity Recognition from User- Annotated Acceleration Data, in Proc. Int'l Conf. Pervasive Comp. 2004: p. 1-17.

[30] Lester, J., et al., A Hybrid Discriminative/Generative Approach for Modeling Human Activities, in Proc. Int'l Joint Conf. on Artificial Intelligence. 2005: p. 766-772.

[31] Lukowicz, P., et al., Recognizing Workshop Activity Using Body Worn Microphone and Accelerometers, in Proc. Int'l Conf. Pervasive Comp. 2004: p. 18-32.

[32] Maurer, U., et al., Activity Recognition and Monitoring Using Multiple Sensors on Different Body Positions, in Proc. Intl Workshop on Wearable and Implantable Body Sensor Networks. 2006, p. 113-116.

[33] Keytel L R1, Goedecke J H, Noakes T D, Hiiloskorpi H, Laukkanen R, van der Merwe L, Lambert EV. Prediction of energy expenditure from heart rate monitoring during submaximal exercise. J Sports Sci. 2005 March; 23(3):289-97.

[34] Rennie K L1, Hennings S J, Mitchell J, Wareham N J. Estimating energy expenditure by heart-rate monitoring without individual calibration. Med Sci Sports Exerc. 2001 June; 33(6):939-45.

[35] J. R. Karp, "HR training for improved running performance," Track Coach, Track and Field News, USA, pp. 5035-5039, 2001.

[36] L. Somanathan, and I. Khalil, "Fitness monitoring system based on HR and Sp02 level," Proc. of the 10th IEEE International Conference on ITAB, Corfu, pp. 1-5, November, 2010.

[37] Marc D. Breton, Sue A. Brown, Colleen Hughes Karvetski, Laura Kollar, Katarina A. Topchyan, Stacey M. Anderson, and Boris P. Kovatchev Adding Heart Rate Signal to a Control-to-Range Artificial Pancreas System Improves the Protection Against Hypoglycemia During Exercise in Type 1 Diabetes DIABETES TECHNOLOGY & THERAPEUTICS Volume 16, Number 8, 2014 $^a$ Mary Ann Liebert, Inc. DOI: 10.1089/dia.2013.0333

[38] J. Parkka, M. Ermes, P. Korpipaa, J. Mantyjarvi, J. Peltola, and I. Korhonen, "Activity Classification Using Realistic Data from Wearable Sensors," IEEE Trans. Information Technology in Biomedicine, vol. 10, no. 1, pp. 119-128, January 2006.

[39] E. M. Tapia and S. Intille, "Real-Time Recognition of Physical Activities and Their Intensities Using Wireless Accelerometers and a Heart Rate Monitor," Proc. Int'l Symp. Wearable Computers (ISWC), pp. 1-4, 2007

[40] Matthew Stenerson, Fraser Cameron, Darrell M. Wilson, Breanne Harris, Shelby Payne , B. Wayne Bequette, and Bruce A. Buckingham, The Impact of Accelerometer and Heart Rate Data on Hypoglycemia Mitigation in Type 1 Diabetes, Journal of Diabetes Science and Technology 2014, Vol. 8(1) 64-69 ©2014 Diabetes Technology Society DOI: 10.1177/ 1932296813516208

[41] Matthew Stenerson, Fraser Cameron, Shelby R. Payne, Sydney L. Payne, Trang T. Ly, MBBS, FRACP, Darrell M. Wilson, Bruce A. Buckingham, The Impact of Accelerometer Use in Exercise-Associated Hypoglycemia Prevention in Type 1 Diabetes. J Diabetes Sci Technol Sep. 17, 2014 1932296814551045

[42] S. D. Patek, L. Magni, E. Dassau, C. Hughes-Karvetski, C. Toffanin, G. De Nicolao, S. Del Favero, M. Breton, C. Dalla Man, E. Renard, H. Zisser, F. J. Doyle, III, C. Cobelli, and B. P. Kovatchev, and International Artificial Pancreas (iAP) Study GroupModular Closed-Loop Control of Diabetes, IEEE TRANSACTIONS ON BIOMEDICAL ENGINEERING, VOL. 59, NO. 11, NOVEMBER 2012

[43] Buckingham B, Cobry E, Clinton P, Gage V, Caswell K, Kunselman E, Cameron F, Chase HP. Preventing hypoglycemia using predictive alarm algorithms and insulin pump suspension. Diabetes Technol Therapeutics 2009; 11(2):93-97.

[44] Cengiz E, Swan K L, Tamborlane W V, Steil G M, Steffen A T, Weinzimer S A. Is an automatic pump suspension feature safe for children with type 1 diabetes? An exploratory analysis with closed-loop system. Diabetes Technol Therapeutics 2009; 11(4):207-210.

[45] Zisser H, Robinson L, Bevier W, Dassau E, Ellingsen C, Doyle F J III, Jovanovic L. Bolus calculator: A review of four "smart" insulin pumps. Diabetes Technol Ther 2008; 10(6): 441-444. [PubMed: 19049372]
[46] Patek, S D.; Breton, M D.; Hughes, C.; Kovatchev, B P. Control of hypoglycemia via estimation of active insulin, glucose forecasts, and risk-based insulin reduction. Proc. 2nd Advanced Technol. Treatment for Diabetes; Athens, Greece. 2009.
[47] Kowalski AJ. Can we really close the loop and how soon? Accelerating the availability of an artificial pancreas: A roadmap to better diabetes outcomes. Diabetes Technol Therapeutics 2009; 11:S113-S119.
[48] Boris P. Kovatchev, PHD1, Erik Otto, MBA2, Daniel Cox, PHD1,Linda Gonder-Frederick, PHD1 and William Clarke, M D, "Evaluation of a New Measure of Blood Glucose Variability in Diabetes",10.2337/dc06-1085Diabetes Care November 2006 vol. 29 no. 11 2433-2438.

The devices, systems, non-transitory computer readable medium, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

a. U.S. patent application Ser. No. 14/419,375 entitled "Computer Simulation for Testing and Monitoring of Treatment Strategies for Stress Hyperglycemia", filed Feb. 3, 2015.
b. International Patent Application No. PCT/US2013/053664 entitled "Computer Simulation for Testing and Monitoring of Treatment Strategies for Stress Hyperglycemia", filed Aug. 5, 2013; International Patent Application Publication No. WO 2014/022864, Feb. 6, 2014.
c. International Patent Application No. PCT/US2015/010167 entitled "Central Data Exchange Node For System Monitoring and Control of Blood Glucose Levels in Diabetic Patients", filed Jan. 5, 2015.
d. International Patent Application No. PCT/US2014/045393 entitled "Simulation of Endogenous and Exogenous Glucose/Insulin/Glucagon Interplay in Type 1 Diabetic Patients", filed Jul. 3, 2014.
e. U.S. patent application Ser. No. 14/266,612 entitled "Method, System and Computer Program Product for Real-Time Detection of Sensitivity Decline in Analyte Sensors", filed Apr. 30, 2014; U.S. Patent Application Publication No. 2014/0244216, Aug. 28, 2014.
f. U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.
g. International Patent Application No. PCT/US2007/082744 entitled "Method, System and Computer Program Product for Real-Time Detection of Sensitivity Decline in Analyte Sensors", filed Oct. 26, 2007; International Patent Application Publication No. WO/2008/052199, May 2, 2008.
h. U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.
i. U.S. patent application Ser. No. 14/241,383 entitled "Method, System and Computer Readable Medium for Adaptive Advisory Control of Diabetes", filed Feb. 26, 2014.
j. International Patent Application No. PCT/US2012/052422 entitled "Method, System and Computer Readable Medium for Adaptive Advisory Control of Diabetes", filed Aug. 26, 2012; International Patent Application Publication No. WO 2013/032965, Mar. 7, 2013.
k. International Patent Application No. PCT/US2014/017754 entitled "Method and System for Model-Based Tracking of Changes in Average Glycemia in Diabetes", filed Feb. 21, 2014; International Patent Application Publication No. WO 2014/130841, Aug. 28, 2014.
l. U.S. patent application Ser. No. 14/128,922 entitled "Unified Platform For Monitoring and Control of Blood Glucose Levels in Diabetic Patients", filed December 23, 2013; U.S. Patent Application Publication No. 2015/0018633, Jan. 15, 2015.
m. International Patent Application No. PCT/US2012/043910 entitled "Unified Platform For Monitoring and Control of Blood Glucose Levels in Diabetic Patients", filed Jun. 23, 2012; International Patent Application Publication No. WO 2012/178134, Dec. 27, 2012.
n. U.S. patent application Ser. No. 14/128,811 entitled "Methods and Apparatus for Modular Power Management and Protection of Critical Services in Ambulatory Medical Devices", filed Dec. 23, 2013; U.S. Patent Application Publication No. 2014/0215239, Jul. 31, 2014.
o. International Patent Application No. PCT/US2012/043883 entitled "Methods and Apparatus for Modular Power Management and Protection of Critical Services in Ambulatory Medical Devices", filed Jun. 22, 2012; International Patent Application Publication No. WO 2012/178113, Dec. 27, 2012.
p. U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013.
q. U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.
r. International Patent Application No. PCT/US2010/025405 entitled "CGM-Based Prevention of Hypoglycemia via Hypoglycemia Risk Assessment and Smooth Reduction Insulin Delivery", filed Feb. 25, 2010; International Patent Application Publication No. WO 2010/099313, Sep. 2, 2010.
s. International Patent Application No. PCT/US2013/042745 entitled "Insulin-Pramlintide Compositions and Methods for Making and Using Them", filed May 24, 2013; International Application Publication No. WO 2013/177565, Nov. 28, 2013.
t. U.S. patent application Ser. No. 13/637,359 entitled "Method, System, and Computer Program Product for Improving the Accuracy of Glucose Sensors Using Insulin Delivery Observation in Diabetes", filed Sep. 25, 2012; U.S. Patent Application Publication No. 2013/0079613, Mar. 28, 2013.
u. International Patent Application No. PCT/US2011/029793 entitled "Method, System, and Computer Program Product for Improving the Accuracy of Glucose Sensors Using Insulin Delivery Observation in Diabetes", filed Mar. 24, 2011; International Patent Application Publication No. WO 2011/119832, Sep. 29, 2011.
v. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; U.S. Patent Application Publication No. 2013/0116649, May 9, 2013.

w. International Patent Application No. PCT/US2011/028163 entitled "Method and System for the Safety, Analysis, and Supervision of Insulin Pump Action and Other Modes of Insulin Delivery in Diabetes", filed Mar. 11, 2011; International Patent Application Publication No. WO 2011/112974, Sep. 15, 2011.

x. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012.

y. International Patent Application No. PCT/US2010/047711 entitled "Tracking the Probability for Imminent Hypoglycemia in Diabetes from Self-Monitoring Blood Glucose (SMBG) Data", filed Sep. 2, 2010; International Patent Application Publication No. WO 2011/028925, Mar. 10, 2011.

z. U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; U.S. Patent Application Publication No. 2012/0245556, Sep. 27, 2012.

aa. International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; International Application Publication No. WO 2011/028731, Mar. 10, 2011.

bb. U.S. patent application Ser. No. 13/380,839 entitled "System, Method, and Computer Simulation Environment for In Silico Trials in Pre-Diabetes and Type 2 Diabetes", filed Dec. 25, 2011; U.S. Patent Application Publication No. 2012/0130698, May 24, 2012.

cc. International Patent Application No. PCT/US2010/040097 entitled "System, Method, and Computer Simulation Environment for In Silico Trials in Prediabetes and Type 2 Diabetes", filed Jun. 25, 2010; International Application Publication No. WO 2010/151834, Dec. 29, 2010.

dd. U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012.

ee. International Patent Application No. PCT/US2010/036629 entitled "System Coordinator and Modular Architecture for Open-Loop and Closed-Loop Control of Diabetes", filed May 28, 2010; International Patent Application Publication No. WO 2010/138848, Dec. 2, 2010.

ff. U.S. patent application Ser. No. 13/131,467 entitled "Method, System, and Computer Program Product for Tracking of Blood Glucose Variability in Diabetes", filed May 26, 2011; U.S. Patent Application Publication No. 2011/0264378, Oct. 27, 2011.

gg. International Patent Application No. PCT/US2009/065725 entitled "Method, System, and Computer Program Product for Tracking of Blood Glucose Variability in Diabetes", filed Nov. 24, 2009; International Patent Application Publication No. WO 2010/062898, Jun. 3, 2010.

hh. U.S. patent application Ser. No. 12/975,580 entitled "Method, System, and Computer Program Product for the Evaluation of Glycemic Control in Diabetes from Self-Monitoring Data", filed Dec. 22, 2010; U.S. Patent Application Publication No. 2012/0004512, Jan. 5, 2012.

ii. U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

jj. U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

kk. International Patent Application No. PCT/US2001/009884 entitled "Method, System, and Computer Program Product for the Evaluation of Glycemic Control in Diabetes", filed Mar. 29, 2001; International Application Publication No. WO 2001/72208, Oct. 4, 2001.

ll. U.S. patent application Ser. No. 12/674,348 entitled "Method, Computer Program Product and System for Individual Assessment of Alcohol Sensitivity", filed Feb. 19, 2010; U.S. Patent Application Publication No. 2011/0264374, Oct. 27, 2011.

mm. International Patent Application No. PCT/US2008/073738 entitled "Method, Computer Program Product and System for Individual Assessment of Alcohol Sensitivity", filed Aug. 20, 2008; International Patent Application Publication No. WO 2009/026381, Feb. 26, 2009.

nn. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; U.S. Patent Application Publication No. 2010/0198520, Aug. 5, 2010.

oo. International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; International Patent Application Publication No. WO 2009/009528, Jan. 15, 2009.

pp. U.S. patent application Ser. No. 12/664,444 entitled "Method, System and Computer Simulation Environment for Testing of Monitoring and Control Strategies in Diabetes", filed Dec. 14, 2009; U.S. Patent Application Publication No. 2010/0179768, Jul. 15, 2010.

qq. International Patent Application No. PCT/US2008/067725 entitled "Method, System and Computer Simulation Environment for Testing of Monitoring and Control Strategies in Diabetes", filed Jun. 20, 2008; International Patent Application Publication No. WO 2008/157781, Dec. 24, 2008.

rr. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

ss. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; International Patent Application Publication No. WO2008/067284, Jun. 5, 2008.

tt. U.S. patent application Ser. No. 12/159,891 entitled "Method, System and Computer Program Product for Evaluation of Blood Glucose Variability in Diabetes from Self-Monitoring Data", filed Jul. 2, 2008; U.S. Patent Application Publication 2009/0171589, Jul. 2, 2009.

uu. International Patent Application No. PCT/US2007/000370 entitled "Method, System and Computer Program Product for Evaluation of Blood Glucose Variability in Diabetes from Self-Monitoring Data", filed Jan. 5, 2007; International Application Publication No. WO 2007/081853, Jul. 19, 2007.

vv. U.S. patent application Ser. No. 12/065,257 entitled "Accuracy of Continuous Glucose Sensors", filed Feb. 28, 2008; U.S. Patent Application Publication No. 2008/0314395, Dec. 25, 2008.

ww. International Patent Application No. PCT/US2006/033724 entitled "Method for Improvising Accuracy of Continuous Glucose Sensors and a Continuous Glucose Sensor Using the Same", filed Aug. 29, 2006; International Application Publication No. WO 2007027691, Mar. 8, 2007.

xx. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; U.S. Patent Application Publication No. 2008/0154513, Jun. 26, 2008.

yy. U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.

zz. International Patent Application No. US2005/013792 entitled "Method, System and Computer Program Product for Evaluating the Accuracy of Blood Glucose Monitoring Sensors/Devices", filed Apr. 21, 2005; International Application Publication No. WO 2005/106017, Nov. 10, 2005.

aaa. U.S. patent application Ser. No. 10/592,883 entitled "Method, Apparatus, and Computer Program Product for Stochastic Psycho-physiological Assessment of Attentional Impairments", filed Sep. 15, 2006; U.S. Pat. No. 7,761,144, issued Jul. 20, 2010.

bbb. U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013.

ccc. International Patent Application No. PCT/US2003/025053 entitled "Managing and Processing Self-Monitoring Blood Glucose", filed Aug. 8, 2003; International Application Publication No. WO 2001/72208, Oct.r 4, 2001.

ddd. International Patent Application No. PCT/US2002/005676 entitled "Method and Apparatus for the Early Diagnosis of Subacute, Potentially Catastrophic Illness", filed Feb. 27, 2002; International Application Publication No. WO 2002/67776, Sep. 6, 2002.

eee. U.S. patent application Ser. No. 09/793,653 entitled "Method and Apparatus for the Early Diagnosis of Subacute, Potentially Catastrophic Illness", filed Feb. 27, 2001; U.S. Patent No. 6,804,551, issued Oct. 12, 2004.

fff. U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005.

ggg. International Patent Application No. PCT/US00/22886 entitled "METHOD AND APPARATUS FOR PREDICTING THE RISK OF HYPOGLYCEMIA", filed Aug. 21, 2000; International Application Publication No. WO 2001/13786, Mar. 1, 2001.

hhh. U.S. patent application Ser. No. 12/665,420 entitled "LQG Artificial Pancreas Control System and Related Method", filed Dec.18, 2009; U.S. Patent Application Publication No. 2010/0249561, Sep. 30, 2010.

iii. International Patent Application No. PCT/US2008/067723 entitled "LQG Artificial Pancreas Control System and Related Method", filed Jun. 20, 2008; International Patent Application Publication No. WO 2008/157780, Dec. 24, 2008.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A method for predicting hypoglycemia for a user comprising:
    obtaining a blood glucose signal (BGstart), a ratio of absolute insulin on board over total daily insulin signal ($IOB_{abs}$/TDI), and an initial glycemic slope signal (S0);
    determining a hypoglycemia risk signal with a hypoglycemia prediction algorithm that determines the probability of the user being hypoglycemic during or after exercise based on the blood glucose signal, the ratio of absolute insulin on board over total daily insulin signal, and the initial glycemic slope signal; and
    determining a hypoglycemia risk state with a classifier algorithm that classifies the hypoglycemia risk signal to identify an actionable hypoglycemia risk state based on a predefined threshold.

2. The method of claim 1, wherein the hypoglycemia prediction algorithm is:

$$Logit(P) = \beta 0 + \beta_1 \cdot BG_{start} + \beta_2 \cdot \frac{IOB_{abs}}{TDI} + \beta_3 \cdot S_0$$

$$\text{Where } \begin{cases} Logit(P) = Log\left(\frac{P}{1-P}\right) \\ P = \frac{e^{\beta 0 + \beta_1 \cdot BG_{start} + \beta_2 \cdot \frac{IOB_{abs}}{TDI} + \beta_3 \cdot S_0}}{1 + e^{\beta 0 + \beta_1 \cdot BG_{start} + \beta_2 \cdot \frac{IOB_{abs}}{TDI} + \beta_3 \cdot S_0}} \end{cases}$$

wherein $\beta 0$, $\beta_1$, $\beta_2$, and $\beta_3$ are predetermined constants.

3. The method of claim 2, wherein the classifier algorithm is:

$$Logit(P) = \begin{cases} 1, & Logit(P) \geq DET_{thresh} \\ 0, & Logit(P) < DET_{thresh} \end{cases}$$

wherein $DET_{thresh}$ is a predetermined constant.

4. The method of claim 3, wherein $DET_{thresh}$ is 0.4.

5. The method of claim 1, wherein the initial glycemic slope signal is obtained based on the blood glucose signal.

6. The method of claim 1 further comprising: generating an alert if the hypoglycemia risk state indicates a risk of hypoglycemia during or after exercise.

7. The method of claim 6 comprising:
    displaying the generated alert on a display of a portable computing device.

8. The method of claim 1 further comprising:
    communicating an instruction to an insulin pump if the hypoglycemic risk state indicates a risk of hypoglycemia during or after exercise.

9. The method of claim 1 further comprising:
    communicating an instruction to the user to consume a determined amount of carbohydrate prior to or during the exercise if the hypoglycemia risk state indicates a risk of hypoglycemia during or after exercise.

10. The method of claim 1 further comprising:
    communicating an instruction to a pump containing glucose raising drugs (e.g. glucagon) if the hypoglycemic risk state indicates a risk of hypoglycemia during or after exercise.

11. The method of claim 1 further comprising:
    obtaining an activity signal from at least one sensor configured to detect when the user begins to exercise.

12. The method of claim 10, wherein the at least one sensor includes one or more of a heartrate sensor and an accelerometer.

13. The method of claim 10 further comprising:
    in response to detecting that the user has begun to exercise, generating an alert if the hypoglycemia risk state indicates a risk of hypoglycemia during or after exercise.

14. The method of claim 1 further comprising:
    obtaining from the user one or more additional signals corresponding to a type of exercise, an intensity of exercise, or a duration of exercise, and wherein the hypoglycemic prediction algorithm determines the probability of the user being hypoglycemic during or after exercise based at least in part on the one or more additional signals.

15. The method of claim 1 wherein obtaining the blood glucose signal comprises receiving the blood glucose signal from a continuous blood glucose monitor.

16. A system for predicting exercise-induced hypoglycemia for a user comprising:
    a digital processor; and
    an exercise module in communication with the digital processor, configured to receive a blood glucose signal (BGstart), a ratio of absolute insulin on board over total daily insulin signal ($IOB_{abs}$/TDI), and an initial glycemic slope signal (S0), wherein the exercise module is further configured to generate a hypoglycemia risk signal with a hypoglycemia prediction algorithm that determines the probability of the user being hypoglycemic during or after exercise based on the blood glucose signal, the ratio of absolute insulin on board over total daily insulin signal, and the initial glycemic slope signal, and is further configured to determine a hypoglycemia risk state with a classifier algorithm that classifies the hypoglycemia risk signal to identify an actionable hypoglycemia risk state based on a predefined threshold.

17. The system of claim 16, wherein the hypoglycemia prediction algorithm is:

$$Logit(P) = \beta 0 + \beta_1 \cdot BG_{start} + \beta_2 \cdot \frac{IOB_{abs}}{TDI} + \beta_3 \cdot S_0$$

$$\text{Where } \begin{cases} Logit(P) = Log\left(\frac{P}{1-P}\right) \\ P = \frac{e^{\beta 0 + \beta_1 \cdot BG_{start} + \beta_2 \cdot \frac{IOB_{abs}}{TDI} + \beta_3 \cdot S_0}}{1 + e^{\beta 0 + \beta_1 \cdot BG_{start} + \beta_2 \cdot \frac{IOB_{abs}}{TDI} + \beta_3 \cdot S_0}} \end{cases}$$

wherein $\beta 0$, $\beta_1$, $\beta_2$, and $\beta_3$ are predetermined constants.

18. The system of claim 16, wherein the classifier algorithm is:

$$Logit(P) = \begin{cases} 1, & Logit(P) \geq DET_{thresh} \\ 0, & Logit(P) < DET_{thresh} \end{cases}$$

wherein $DET_{thresh}$ is a predetermined constant.

19. The system of claim 16 comprising:
a display; and wherein the digital processor is configured to generate an alert on the display if the hypoglycemia risk state indicates a risk of hypoglycemia during or after exercise.

20. The system of claim 16 comprising: a continuous blood glucose monitoring sensor in communication with the digital processor, the continuous blood glucose monitoring sensor configured to generate the blood glucose signal.

21. The system of claim 19 further comprising:
an insulin pump in communication with the digital processor and configured to dispense or not dispense insulin in response the determined hypoglycemia risk state.

* * * * *